United States Patent
Finarov et al.

(12)

(10) Patent No.: US 6,731,963 B2
(45) Date of Patent: May 4, 2004

(54) DEVICE FOR ENHANCEMENT AND QUALITY IMPROVEMENT OF BLOOD-RELATED SIGNALS FOR USE IN A SYSTEM FOR NON-INVASIVE MEASUREMENTS OF BLOOD-RELATED SIGNALS

(75) Inventors: Alexander Finarov, Rehovot (IL); Ilya Fine, Rehovot (IL)

(73) Assignee: Orsense Ltd., Rehovot (IL)

( * ) Notice: Subject to any disclaimer, the term of this patent is extended or adjusted under 35 U.S.C. 154(b) by 0 days.

(21) Appl. No.: 09/948,900

(22) Filed: Sep. 7, 2001

(65) Prior Publication Data

US 2002/0077535 A1 Jun. 20, 2002

(30) Foreign Application Priority Data

Mar. 9, 1999 (IL) ................................. 128903
May 5, 1999 (IL) ................................. 129790

(51) Int. Cl.⁷ ................................. A61B 5/00
(52) U.S. Cl. ........................ 600/335; 600/322
(58) Field of Search ................ 600/322–323, 600/335, 334, 344

(56) References Cited

U.S. PATENT DOCUMENTS

| | | | | |
|---|---|---|---|---|
| 2,438,901 A | * | 4/1948 | Coxe | 2/21 |
| 4,825,872 A | | 5/1989 | Tan et al. | |
| 4,865,038 A | * | 9/1989 | Rich et al. | 600/344 |
| 5,007,423 A | * | 4/1991 | Branstetter et al. | 600/334 |
| 5,101,825 A | | 4/1992 | Gravenstein et al. | |
| 5,170,786 A | | 12/1992 | Thomas et al. | |
| 5,247,931 A | * | 9/1993 | Norwood | 600/344 |
| 5,337,744 A | * | 8/1994 | Branigan | 600/407 |
| 5,452,717 A | | 9/1995 | Branigan et al. | |
| 5,483,697 A | * | 1/1996 | Fuchs | 2/161.7 |
| 5,499,627 A | | 3/1996 | Steuer et al. | |
| 5,638,816 A | | 6/1997 | Kiani-Azarbayjany et al. | |
| 5,919,133 A | * | 7/1999 | Taylor et al. | 600/323 |
| 6,222,189 B1 | * | 4/2001 | Misner et al. | 600/335 |
| 6,292,686 B1 | * | 9/2001 | Chaiken et al. | 600/476 |

FOREIGN PATENT DOCUMENTS

| | | |
|---|---|---|
| DE | 196 29 342 A1 | 1/1998 |
| EP | 0 313 238 A2 | 4/1989 |
| WO | WO 98/03847 | 1/1998 |
| WO | WO 98/43096 | 10/1998 |
| WO | WO 99/55222 | 11/1999 |
| WO | WO 99/65384 | 12/1999 |

* cited by examiner

*Primary Examiner*—Mak F. Hindenbrug
*Assistant Examiner*—Matthew Kremer
(74) *Attorney, Agent, or Firm*—Fitch, Even, Tabin & Flannery

(57) ABSTRACT

A disposable device is presented aimed at enhancing blood-related signals and improving their quality during non-invasive measurements of blood parameters. The device is applicable to a patient's finger or toe, and comprises a cover for wrapping at least a part of the finger or toe including a tip portion thereof in a manner to provide even pressurization of tissue within the wrapped portion with a pressure less than a systolic pressure. This results in enhancement and quality improvement of the measured blood-related signal. The cover is elastic and is shiftable along a longitudinal axis of the finger or toe between an inoperative folded position of the cover and an operative extracted position of the cover, in which it wraps the finger or toe portion including the tip portion and provides said even pressurization of the entire wrapped tissue. At least a portion of the cover is made of a material enabling the non-invasive measurements of the blood-related signal therethrough.

26 Claims, 4 Drawing Sheets

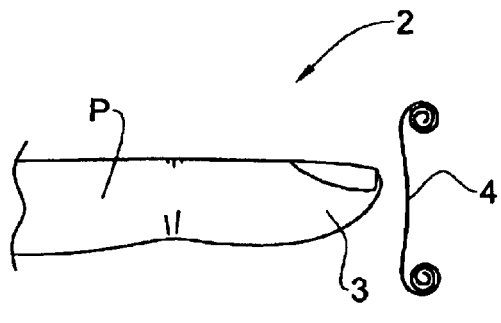
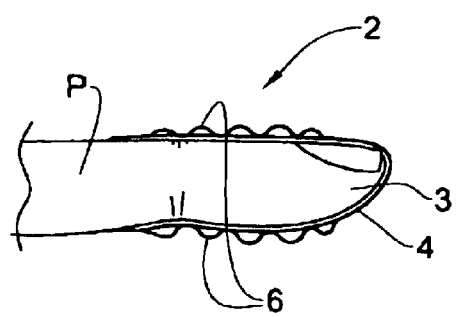
FIG. 1A  FIG. 1B
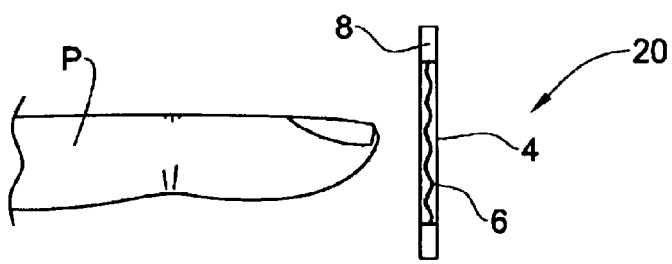
FIG. 2A
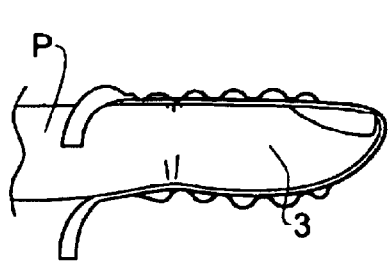
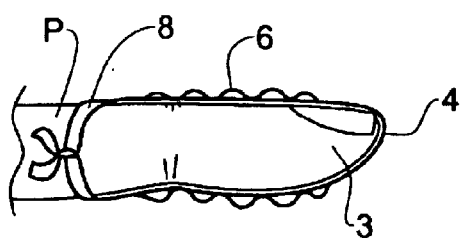
FIG. 2B  FIG. 2C

DEVICE FOR ENHANCEMENT AND QUALITY IMPROVEMENT OF BLOOD-RELATED SIGNALS FOR USE IN A SYSTEM FOR NON-INVASIVE MEASUREMENTS OF BLOOD-RELATED SIGNALS

This is a continuation-in-part, of prior application number PCT/IL99/00621 filed Nov. 18, 1999 designating the United States and claiming priority from Israel Patent Applications 128903 filed Mar. 9, 1999 and 129790 filed May 5, 1999, which are hereby incorporated herein by reference in their entirety.—The entire disclosure of the prior application, from which a copy of the oath or declaration is supplied under paragraph 3 below, is considered as being part of the disclosure of the accompanying application, and is hereby incorporated by reference therein.

FIELD OF THE INVENTION

The present invention is in the field of non-invasive measurements of physiological parameters of patients, and relates to a device for the enhancement and quality improvement of blood-related signals.

BACKGROUND OF THE INVENTION

Non-invasive methods for measuring various blood-related parameters have become very popular due to the fact that these measurements, in distinction to invasive ones, do not involve the physical withdrawal of a blood sample from the patient's body. Non-invasive measurements are based on the pulsatile nature of arterial blood, and utilize optical monitoring techniques capable of detecting such pulsatile blood behavior. Results obtained from pulse measurements can be used for determining various physiological parameters such as blood oxygen saturation, hematocrit, the concentration of hemoglobin, glucose, carbon dioxide, arterial blood pressure, etc.

The optical monitoring techniques of the kind specified typically utilize the detection of light transmitted or reflected from different locations on a patient's body. According to some of these techniques, disclosed for example in U.S. Pat. No. 5,101,825 changes in the blood parameters at a specific location are measured as a function of changes in the blood volume at this location. Other techniques, disclosed for example in U.S. Pat. No. 5,499,627, utilize impedance measurements.

Various methods aimed at increasing the natural pulsatile signal of a patient for effecting non-invasive optical measurements have been developed. These methods are disclosed for example in the following patent documents: DE 19629342, U.S. Pat. No. 5,638,816. WO 9843096 and in U.S. patent application Ser. No. 09/468,178, which is a co-pending application assigned to the assignee of the present application.

According to the above methods, the natural pulse signals are either detected and used for measurements, or created by performing various suitable procedures which are typically based on the use of a probe applied to the patient's finger (pulse oximetry) or other extremities. These methods typically require well-established, stable and reproducible capillary, venous and arterial blood presence at the location under measurement. As known, to meet such a requirement, a slight pressure may be applied to the soft tissue in the vicinity of the measurement location. A pressure-inducing holder used in such a measurement probe is usually a part of the probe itself, i.e., is associated with a specific sensor used in a specific measurement device.

Some of the conventional measuring devices utilize folded adhesive sensors, namely disposable adhesive sensors with optics embedded therein. For example, U.S. Pat. No. 5,170,786 discloses a reusable probe system aimed at enabling to reuse the sensor element, which are the most expensive part of a probe system, and dispose a positioning substrate. In this probe system, the sensor elements are thus made separable from the flexible substrate, which is to be brought into contact with the patient's skin, and is formed with apertures to fasten a light source and light sensor in stable disposition on the skin. EP 0313238 discloses a pulse oximeter sensor constructed so as to reduce signal loss due to thermal vasoconstriction and ambient light interference. The sensor utilizes a wrap of a disposable elongated configuration and includes a sheet of metalized material. A light source and a detector are aligned with the wrap.

U.S. Pat. No. 5,452,717 discloses a sensor probe, in which a source of electromagnetic radiation and a detector are supported on a carrier having a flexible body to at least partially surround a portion of the tissue under measurements All elastic sheath is coupled to the carrier by its one end, and has the other end of a tubular shape rollable upon itself to surround at least a portion of the carrier, with the carrier positioned over the portion of tissue.???

Other devices utilize non-disposable sensors in the form of a clip to be placed on the patient's finger and fixed by a spring. Elastic cushions support the optical elements and prevent slipping of the sensors off the finger.

SUMMARY OF THE INVENTION

The inventors have found that the application of homogeneous, even pressure to a body part to which measurements are to be applied results in the enhancement and quality improvement of blood-related signals from the body part. However, the existing disposable devices fail to provide homogeneous pressure applied to the patient's finger. As a result, even pressurization of the finger tissue cannot be achieved. Furthermore, none of the existing devices can be used solely for the enhancement and quality improvement of blood-related signals, regardless of the measurement technique being used. For example, adhesive sensors are applicable to the pulse-oximetry technique based on the detection of optical signals, while being unsuitable for the impedance-based or a similar technique.

A pressure-inducing element can be applied to the patient's finger prior to the measurement itself, so as to create the required preconditions for starting blood-related measurements. To this end, it is desirable to have a pressure-inducing holder that would be applicable for a patient's finger, irrespective of a patient's individual peculiarities, and that would be useful with a non-invasive measurement device of any kind.

There is accordingly a need in the art to improve conventional techniques for measuring blood-related signals by providing a novel disposable and quickly mountable/removable device for applying to the patient's finger or toe so as to enhance blood-related signal and improve the quality of the signal.

The main idea of the present invention consists of providing such a disposable device, which, when being applied to the patient's finger or toe (i.e., being wrapped around the finger/toe portion), is capable of providing even pressurization of the wrapped portion including the finger/toe tip, and can be used with a sensor of any suitable known kind capable of detecting the blood-related signal to measure any suitable parameter that can be derived therefrom.

There is thus provided according to the invention, a disposable, removable device for applying to a patient's finger or toe for non-invasive measurements of blood-related parameters derived from a response of a measurement location in the finger or toe to a predetermined external field, wherein:

the device comprises a cover for wrapping at least a portion of the finger or toe including a tip portion thereof in a manner to provide even pressurization of the entire wrapped portion with a pressure less than systolic pressure, thereby providing enhancement and quality improvement of measured signals;

said cover is elastic, has a substantially circular cross-section, and is shiftable along a longitudinal axis of the finger or toe between an inoperative folded position of the cover and an operative extracted position of the cover, in which it wraps the finger or toe portion including the tip portion, and provides said even pressurization of the entire wrapped tissue with the pressure being less than systolic pressure;

at least a portion of the cover is made of a material enabling said non-invasive measurements of the blood-related signal therethrough.

The elasticity of the cover may be such that the cover itself desirably presses the finger/toe tissue whilst wrapping the finger/toe portion. Alternatively, or additionally the device may comprise a pneumatic device or a mechanical device, e.g., a pressing ring to be placed on tee finger/toe above the cover. By operating such a device, e.g., by twisting the ring, the desired pressure can be established.

The elasticity of the cover and its small thickness provides slight and even pressurization (which is less than systolic blood pressure) on the tissue within the covered finger portion including the fingertip. This results in the enhancement of the pulsatile and non-pulsatile blood-related signals, prevents blood flow disturbance during measurement, and stabilizes the finger tissue during measurements, thereby improving the quality of the measured signals.

Preferably, the device also provides a heating effect to heat the wrapped finger/toe portion up to a desired temperature (about 38° C.), thereby enhancing the blood-related signal even more The heating ability of the device increases the accuracy of the non-invasively derived blood-related parameters such as blood oxygen saturation, blood pressure, hemoglobin, glucose, cholesterol and other analyte concentrations. The shrinkage effect by heating the cover affects tissue pressurization.

According to another aspect of the present invention, there is provided a method for obtaining enhanced and quality improved blood-related signals from a portion on a patient's body, the method comprising the steps of:

(i) applying a pressure, substantially less than a systolic pressure, to said portion in a manner to provide even pressurization thereof;

(ii) applying sensor means to a measurement location within the pressed portion, the sensor means being capable of applying an external field to said measurement location, detecting a response of the measurement location to said external field indicative of blood-related signals, and generating data representative thereof.

The external field to be applied to the measurement location may be electromagnetic radiation. In his case, the sensor means may utilize an illumination assembly for illuminating the measurement location with incident radiation, e.g., near infra-red (IR) radiation of having a wavelength of 600–2000 mm, and a detection assembly for detecting a light response from the illuminated location. The location of the detection assembly depends on the kind of response that is to be detected, i.e. reflected or transmitted signals.

It should be understood that in order to enable the application of such a radiation-based sensor means, the cover should be formed with means enabling light propagation therethrough. To this end, the entire cover may be transparent with respect to the incident radiation (e.g., near IR radiation). In this case, the cover should be of a sufficient thickness (i.e., practically about 0.1–0.2 mm and preferably not exceeding 50 $\mu$m) so as to prevent collection by the detection assembly of incident radiation rounding the wrapped portion, while allowing the detection of the signal response.

Alternatively when a thicker cover is used (e.g., of 0.5 mm in thickness), the cover may be formed with at least one optical window transparent for near IR radiation, thereby enabling the application of the sensor means to a location within the wrapped portion below the window. If the transmitted signal is to be detected, two optical windows should be provided made at opposite sides of the cover. Should the reflected signal be detected by the sensor means, the provision of only one optical window is sufficient for measurements, but two spaced-apart optical windows located at the same side of the cover can be used. The non-transparent regions of the cover absorb light waves going around the cover' material thickness and through the skin of the wrapped portion, and prevent these waves from being collected by the detection assembly. This increases the signal-to-noise ratio of the detected signal.

The non-transparent regions can be manufactured from the same material as that of the transparent regions, but with additional pigments such as carbon, titanium oxide, BaS, $BaSO_4$, etc. that make these regions non-transparent for near IR radiation. Materials suitable for the manufacture of the cover are silicon, latex and other flexible, elastic and transparent for near IR radiation materials.

More specifically, the present invention is useful with non-invasive measurements on a patient's finger, and is therefore described below with respect to this application

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 1A and 1B illustrate a device, constructed according to one embodiment of the invention, which is, respectively, in an inoperative position prior to being applied to a patient's finger, and in an operative position when being applied to the patient's finger;

FIG. 2A illustrates a device in an inoperative position thereof constructed according to another embodiment of the invention;

FIGS. 2B and 2C illustrate two operational steps for applying the device of FIG. 2A to the patient's finger;

DETAILED DESCRIPTION OF PREFERRED EMBODIMENTS

Figure 3A:
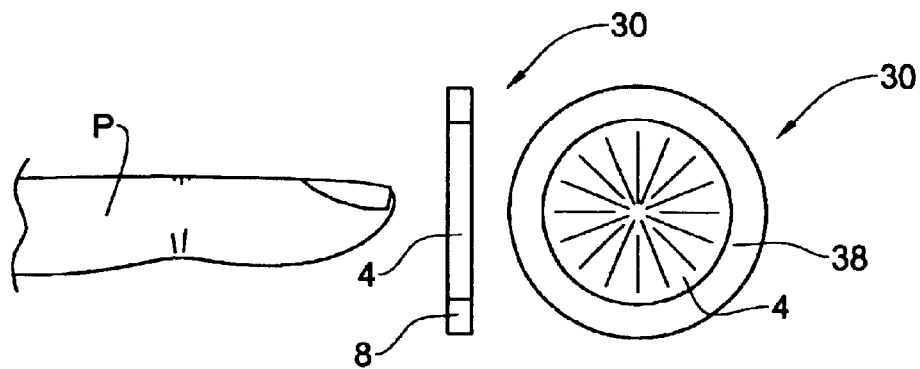
FIG. 3A illustrates a device in an inoperative position thereof constructed according to yet another embodiment of the invention.

Referring to FIGS. 1A and 1B, there is illustrated a device 2 designed so as to be mountable on the patient's finger P in a manner to apply even pressurization of the wrapped portion of the finger including the fingertip 3 with a pressure less than systolic pressure, to thereby enable enhancement of blood-related signals measured as a response of a measurement location within the wrapped finger portion to an external field applied thereto. The device 2 comprises a cover 4, which is rolled up into a spherical-like segment when in an inoperative position of the device 2, i.e., prior to being applied to the finger P (FIG. 1A). To put the device 2 in operation, the cover 4 is unrolled so as to wrap the finger portion including the fingertip 3 (FIG. 1B). To this end, the cover 4 is made of an elastic material, for example rubber, silicone, PVC, polyurethane, polyethylene, of a sufficient thickness so as to be easily shifted from it normally inoperative, folded position into the operative, extracted position, and to be suitable for non-invasive measurements therethrough. If optical measurements are considered, and no specific window or windows are provided in the cover (as will be described more specifically further below with reference to FIGS. 6A–6B), the cover should preferably be of about 0.1–0.2 mm in thickness. If the cover of a larger thickness is used, it is formed with one or two regions (for reflection and transmission mode measurements, respectively) made of a different material to define window (s) for light propagation therethrough.

Such an elastic and thin cover slightly presses the tissue of the finger P. As indicated above, the elasticity of the cover and its small thickness provides slight, regular (uniform) pressurization on the tissue within the covered portion including the fingertip, for example within a range 5–20 mmHg, which is always less than the systolic blood pressure. This slight even pressurization of the tissue, on the one hand, causes the enhancement and quality improvement of the pulsatile and non-pulsatile blood-related signals within the wrapped portion of the finger P, and, on the other hand, prevents blood flow disturbance during future measurements.

The cover 4 is made from such materials that do not affect any particular technique for measuring blood-related parameters. More specifically, for optical, acoustic and impedance-based measuring techniques, the material of the cover should allow for the penetration of, respectively, light, sound or electrical current into the tissue. For example, rubber, silicone, latex, PVC, nylon, paraffin, etc. can be used in the manufacture of the elastic cover It should also be noted, although not specifically shown, that the elastic film-like cover for even pressurization of a finger portion including the fingertip may be formed by disposing quick drying glues such as Poly Vinil Alcohol, some resin solutions or the like, onto the finger. These materials, while drying, form a thin film coating on the finger.

As further shown in FIG. 1B, the device 2 also comprises a heating element 6 located above the extracted cover 4 wrapping the finger P. In this specific example, the heating element 6 is a conductive material (e.g., silicon) appropriately connectable (through contacts) to a power source (not shown) that supplies sufficient voltage, for example, in a range of 1–6 V.

There are several constructional possibilities for implementing a heating effect in the device 2. The heating element 6 malt be a separate constructional part to be applied to the wrapped finger portion at a separate operational step, upon unrolling the cover 4 to wrap the finger portion. The heating element may be made of conductive silicone, conductive clothes, metal wire like NiCr, etc. The heating element may be attached to the cover 4, for example by making the heating element from sufficiently flexible material to allow for rolling/unrolling thereof together with the cover. Heating elements may be implanted into the cover. The material resistance of the cover itself, or the chemical exothermic reaction of two or more components (e.g., polyurethane) applied to the cover, may be utilized as a heating means Thus, the pressuring film-like cover 4 provides even pressurization of the finger portion including the fingertip, by which the enhancement and quality improvement of the blood-related signals can be obtained, while the heating element 6 enhances these signals even more, and increases the accuracy of blood-related parameters that are derived from the measured signals. These blood-related parameters are such as blood oxygen saturation, blood pressure, hemoglobin, glucose, cholesterol and other analytes concentration, etc.

It should, however, be noted that the provision of any heating element is optional. As indicated above, on the one hand, the provision of the heating effect increases the accuracy of the non-invasively derived blood-related parameters, and, on the other hand, the shrinkage caused by heating the cover affects the tissue pressurization.

Reference is now made to FIG. 2A illustrating a device 20 to be applied to the patient's finger P to provide even pressurization of the finger portion including the fingertip to thereby enable enhancement and quality improvement of measured blood-related signals. To facilitate (understanding the same reference numbers are used for identifying those components which are identical in the devices 2 and 20. The device 20 comprises a cover 4, a heating element 6, and a flexible strap 8 (constituting a locking assembly) capable of forming a ring on the finger above the cover, so as to attach the cover to the finger. The cover 4 is in the form of a thin flat film, which is shaped like a circle when in an inoperative position of the device 20. The heating element 6 is designed like a pair of spirals extending along two opposite regions of an outer surface of the film 4. The strap 8 may be made of a flexible wire, or may be a stretchable material, for example, the same as that of the film.

FIGS. 2B and 2C more specifically illustrate the main operational steps for applying the device 20 to the patient's finger P to put the device in operation. The film cover 4 is stretched along the longitudinal axis of the finger, thereby wrapping the finger portion including the fingertip 3 and extending the heating element 6 along the wrapped portion of the finger.

Figure 3B:
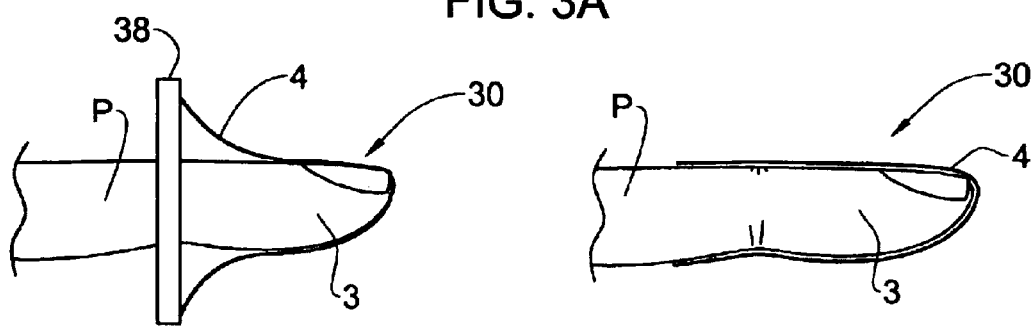
FIGS. 3B and 3C illustrate two operational steps for applying the device of FIG. 3A to the patient's finger.
Figure 3C:
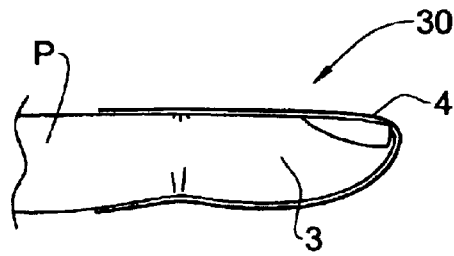

When the cover 4 wraps the finger portion (with the fingertip 3), the opposite ends of the strap 8 are fastened so as to form a ring 8 on the finger above the cover. If the strap 8 is made of a flexible wire, its ends can be twisted together to fix the ring's diameter, thereby applying desired pressure to the finger tissue within the wrapped finger portion (FIG. 2D). Should the stretchable material be used for the strap 8, Velcro-like fasteners or the like would be appropriately provided at the ends of the strap. Obviously, any other suitable technique may be used for providing a ring-like support element 8 on the finger in a manner allowing for varying the ring's diameter FIGS. 3A–3C illustrate a device 30 to be applied to the patient's finger P to provide even pressurization of the finger portion including the fingertip for enhancement and quality improvement of measured blood-related signals. The device 30 is generally similar to the devices 2 and 20, but differing therefrom in that its cover 4, which is made of a high elastic material, is provided with a supporting ring 38 having a preset stretching force. The ring 38 may be made of a plastic material. To stretch the cover for attaching the device 30 to the patient's finger, the ring 38 is mounted onto the finger, and force is applied to the ring 38 to move it along the finger. When the cover 4 is stretched up to a preset maximum value, it forces against the ring 38 and when this force exceeds the preset stretching force of the ring 38, the ring 38 tears off and can be removed from the finger. Hence, the desirably stretched cover 4 wraps the finger portion including the fingertip 3 whilst applying the desired even pressurization thereto.

Figure 4A:
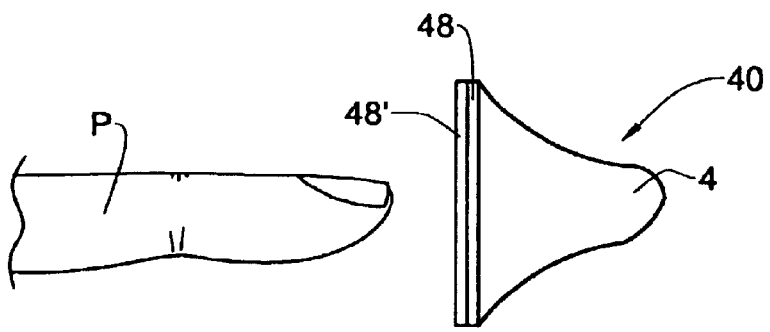
FIGS. 4A to 4C illustrate one more embodiment of the present invention.
Figure 4B:
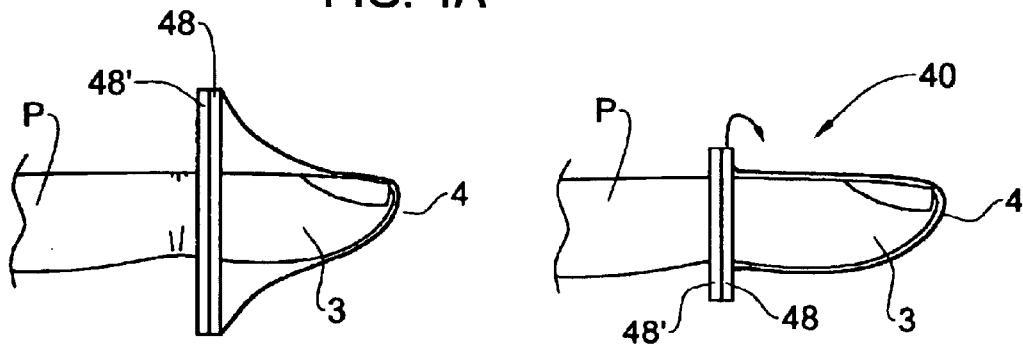
Figure 4C:
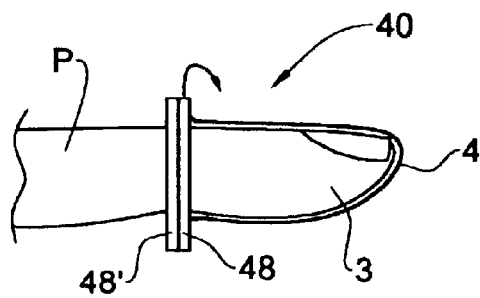

FIGS. 4A–4C illustrate a device 40 constructed according to yet another embodiment of the invention. Similarly, the same reference numbers are used for identifying those components, which are identical in the device 40 and in the previously described examples. Here, in distinction to the device 30, a cover 4 is made of a relatively low elastic material, and a supporting twisting ring 48 and a separate ring are attached to periphery circumferential region 4A of the cover. The ring 48' is made of a suitable material such that the ring 48' is hardly movable along the finger P as compared to the ring 48. The ring 48' may be formed with a slot, rather then being a closed loop, so as to adjust the diameter of the ring 48' and to facilitate its mounting on the finger, after wrapping the finger portion by the cover 4.

Thus, to put the device 40 in operation, the ring 48 is mounted onto the finger P, and moved along the finger from the fingertip, thereby stretching the cover 4. To sufficiently stretch the cover 4 so as to apply the desired pressure to the tissue, the ring 48 is twisted, in a clockwise direction in FIG. 4C, while the ring 48 serves as a locking element preventing the movement of the ring 48 whilst being twisted.

Figure 5A:
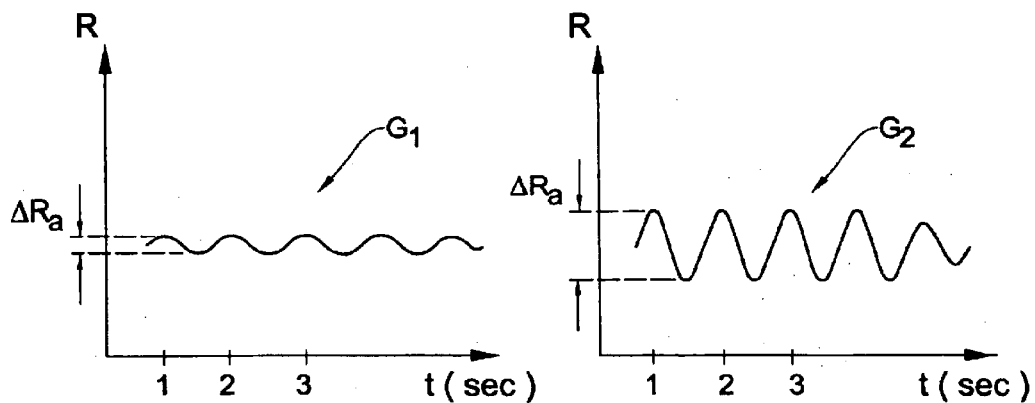
FIGS. 5A to 5C graphically illustrate the main operational principles of the device according to the invention, when being used with, respectively, optical-, impedance- and occlusion-based measurements.
Figure 5B:
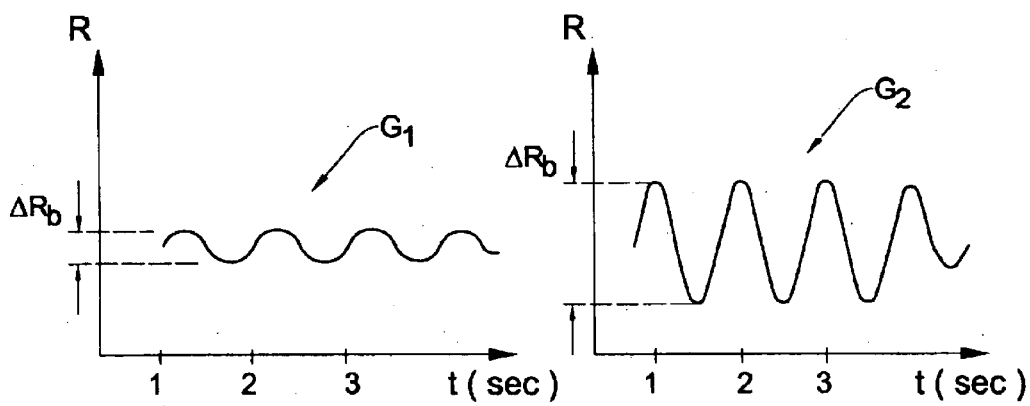
Figure 5C:
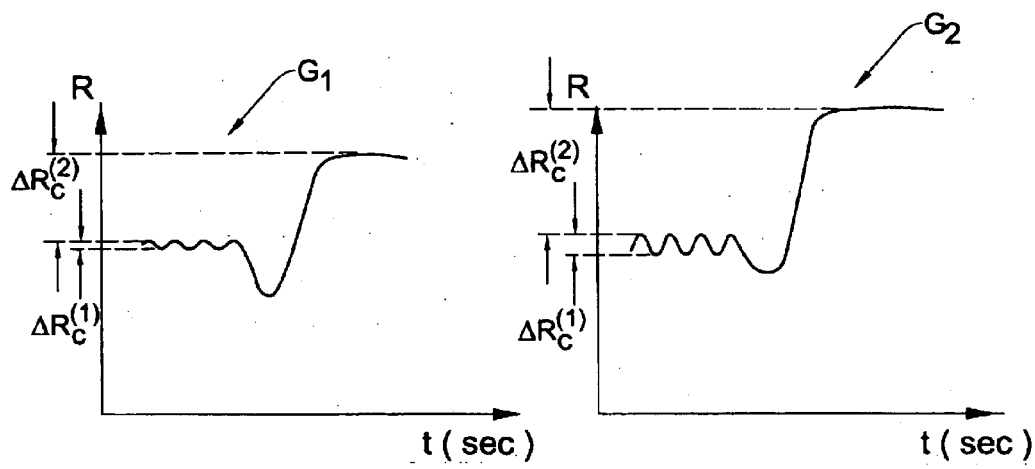

Turning now to FIGS. 5A–5C, there are graphically illustrated the main operational principles of the device of the present invention (which may be constructed as either one of the above-described devices) when being used for, respectively, optical-, impedance- and occlusion-based measurements. Each of these figures illustrates two graphs, $G_1$ and $G_2$, corresponding to the time dependence of the measured blood-related signal R measured without and with the device of the present invention, respectively. These graphs present experimental results obtained whilst performing the respective measurements using known measurement systems. In the optical and occlusion measurements, what actually is measured is the intensity of light transmitted through the patient's finger, R being the light intensity. As for the impedance-based technique, R corresponds to arbitrary units of impedance. As clearly seen in the figures, the application of the device according to the invention enhances the blood-related signal approximately by 2–3 times. More specifically, $\Delta R_a$ are 5% and 10% of the total transmission signal before and after the application of the device, respectively; $\Delta R_b$ are 3% and 6% of the total impedance signal before and after the application of the device, respectively; $\Delta R^{(1)}_c$ and $\Delta R^{(2)}_c$ are, respectively, 5% and 20%, and 10% and 40% of the total transmission signal.

The main principles of the optical- and impedance-based measurements do not form a part of the present invention being known per se, and therefore need not be specifically described. As for the occlusion-based technique, it also does not form a part of the present invention, and is the subject matter of the above-indicated co-pending U.S. patent application, assigned to the assignee of the present application. The main principles underlying the occlusion-based technique utilize the fact that light absorption characteristics of a blood perfuse fleshy medium dramatically changes when the character of the blood flow changes. In distinction to the conventional measuring techniques of the kind specified, e.g., pulse-oximetry, occlusion-based measuring technique deals with non-volumetric blood-related signals. According to the occlusion-based technique, over-systolic pressure is applied to one location on the patient's body to thereby create the state of temporary blood-flow cessation at a measurement location downstream of the location to which the over-systolic pressure is applied (with respect to the blood flow direction), and optical measurements are applied to the measurement location.

As indicated above, such a cover 4 of the pressurizing device according to the invention should be provided with means enabling optical measurements therethrough, based on the detection of either reflected or transmitted light (generally, light response) of the blood perfused medium. In other words, the cover should be constructed so as to enable the light wave-propagation therethrough. If the cover is substantially thin, (i.e., practically having a thickness of about 0.1–0.2 mm and preferably not exceeding 50 μm), the cover can be entirely transparent for predetermined incident radiation, e.g., near IR radiation (600–2000 mm), being made of silicon, latex, etc.

Figure 6A:
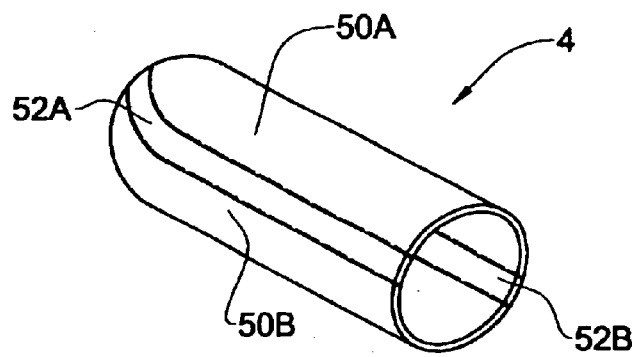
FIGS. 6A to 6C schematically illustrate three more embodiments of a device according to the invention.
Figure 6B:
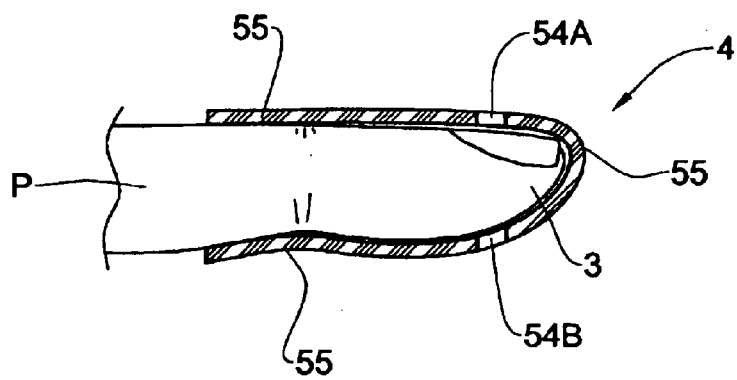
Figure 6C:
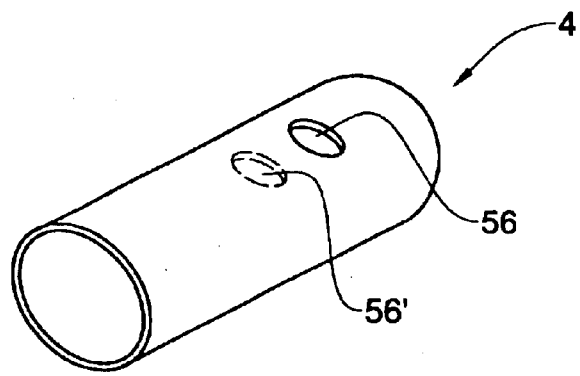

FIGS. 6A–6C illustrate three different examples, respectively, of a cup-like cover to be used in the disposable device according to the invention. In these examples, the cover may be thicker than 0.1–0.2 mm, for example being of 0.5 mm in thickness. Although the cover is illustrated here in the "ready to be mounted on a patient's finger" position, it should be understood that this position may be achieved by unrolling the cover.

According to the example of FIG. 6A, the cover 4 is formed with its upper and lower portion 50a and 50b being made of a material transparent to near IR radiation (e.g., silicon or latex), and two opposite side portions 52a and 52b, being made of a material non-transparent (absorbing) to near IR radiation. This, for example, may be achieved by manufacturing the entire cover from the same transparent material and forming its side portions 52a and 52b with additional pigments such as carbon, titanium oxide, BaS, $BaSO_4$, etc. The provision of the opposite transparent portion 50a and 50b enables the use of such cover 4 with a transmission-based measurement unit. In other words, illumination and detection assemblies of the measurement unit should be associated with the portions 50a and 50b, respectively, or vice versa. The provisions of the portions 52a and 52b between the portions 50a and 50b, which are used for measurements, prevents detection of incident light rounding the finger.

In the example of FIG. 6B, the cover 4 is formed with two opposite optical windows 54a and 54b. The windows are made of a material transparent for near IR radiation, while all the other regions 55 of the covers except for those occupied by the windows, are made of a material non-transparent for near IR radiation. This design of the cover is also suitable for use with a transmission-based measurement unit.

In the example of FIG. 6C, the cover 4 is formed with a single optical window 56. This design is suitable to be used with a reflection-based measurement unit. As shown in the figure, for the purposes of the reflection-based measurement technique, an additional optical window 56' (shown in dashed lines) may be provided being located close to the window 56 at the same side of the cover. The windows 56 and 56' are spaced by a small region of the non-transparent material of the cover.

Those skilled in the art will readily appreciate that various modifications and changes may be applied to the above-described embodiments of the invention without departing from its scope defined in and by the appended claims.

What is claimed is:

1. A disposable device for use in a method of non-invasive measurements of blood-related signals from a portion of a patient's finger or toe, wherein the method includes application of pressure, substantially less than a systolic pressure, to the portion of the patient's finger or toe in a manner provide even pressurization of said portion, application of an external field to a measurement location within the pressed portion, detection of a response of the measurement location to said external field, and generation of data indicative of blood-related signals, the device comprising: a cover for wrapping at least a portion of the finger or toe, to thereby provide the even pressurization of the entire wrapped portion; said cover being elastic, having a substantially circular cross-section, and being shiftable along a longitudinal axis of the finger or toe between an inoperative folded position of the cover and an operative extracted position of the cover, in which the cover wraps the finger or toe portion including tip portion and provides said even pressurization of the entire wrapped tissue with the pressure less than the systolic pressure; at least a portion of the cover being made of a material enabling the non-invasive measurements of the blood-related signal through said at least portion of the cover, said even pressurization of the body portion under measurement provided by the device resulting in that said response is at least two times higher than that obtained with no such even pressurization.

2. The device according to claim 1, wherein said cover in its folded inoperative position presents a rolled spherically-shaped segment, and is unrollable into the operative extracted position thereof to wrap the finger or toe portion including the tip portion.

3. The device according to claim 1, wherein said cover has a flat circular geometry when in the inoperative position thereof, and is stretchable into the operative extracted position thereof to wrap the finger or toe portion including the tip portion.

4. The device according to claim 2, wherein said cover is formed with a locking assembly, which, when in the inoperative position of the cover, extends along at least a part of a circumferential periphery region of the cover.

5. The device according to claim 3, wherein said cover is formed with a locking assembly, which, when in the inoperative position of the cover, extends along at least a part of a circumferential periphery region of the cover.

6. The device according to claim 4, wherein said locking assembly, when in the inoperative position of the cover, is in the form of a strap, which forms a ring when in the operative position of the cover, said strap being flexible to enable twisting of its ends, thereby enabling adjustment of the ring diameter to apply a desired pressure.

7. The device according to claim 5, wherein said locking assembly, when in the inoperative position of the cover, is in the form of a strap, which forms a ring when in the operative position of the cover, said strap being flexible to enable twisting of its ends, thereby enabling adjustment of the ring diameter to apply a desired pressure.

8. The device according to claim 4, wherein said locking assembly is a ring having a preset stretching force and extending along the entire circumferential periphery region of the cover when in the inoperative position thereof, shifting the cover into the operative position thereof resulting in that a force applied to the ring exceeds said preset stretching force, thereby causing tearing off of the ring.

9. The device according to claim 5, wherein said locking assembly is a ring having a preset stretching force and extending along the entire circumferential periphery region of the cover when in the inoperative position thereof, shifting the cover into the operative position thereof resulting in that a force applied to the ring exceeds said preset stretching force, thereby causing tearing off of the ring.

10. The device according to claim 4, wherein said locking assembly comprises first and second rings extending along two successive circumferential regions at the periphery of the cover, the first ring being twistable to stretch the cover, when in the operative position thereof, and the second ring serving as a locking mechanism, preventing movement of said first ring being twisted along the finger or toe.

11. The device according to claim 5, wherein said locking assembly comprises first and second rings extending along two successive circumferential regions at the periphery of the cover, the first ring being twistable to stretch the cover, when in the operative position thereof, and the second ring serving as a locking mechanism, preventing movement of said first ring being twisted along the finger or toe.

12. The device according to claim 1, and also comprising a heating assembly for heating said tissue through said cover.

13. The device according to claim 12, wherein said heating assembly comprises a heating element formed by a conductive material associated with a voltage supply source.

14. The device according to claim 13, wherein said cover in its folded inoperative position presents a rolled spherically-shaped segment, and is unrollable into its operative extracted position to wrap the finger or toe portion including the tip portion;

said heating element is made of flexible material to be shiftable together with the cover between an inoperative rolled position of the heating element and an operative unrolled position of the heating element, in which the heating element is located above the unrolled cover.

15. The device according to claim 1, wherein the entire cover is transparent to predetermined incident radiation used in the non-invasive measurements, the cover being sufficiently thin to prevent the detection of radiation rounding the wrapped portion.

16. The device according to claim 15, wherein said predetermined radiation is sound.

17. The device according to claim 15, wherein said cover is made of a material enabling electrical current to be induced in the wrapped tissue.

18. The device according to claim 15, wherein the cover has a thickness of about 0.1–0.2 mm.

19. The device according to claim 1, wherein said cover is made of at least one material selected from the group including: rubber, silicone, latex, PVC, nylon, paraffin, polyethylene.

20. The device according to claim 1, wherein the cover has two portions thereof made of a material substantially transparent with respect to predetermined radiation, said two portions being surrounded by a material of the cover substantially non-transparent with respect to said predetermined radiation.

21. The device according to claim 20, wherein said two portions are located diametrically opposite to each other.

22. The device according to claim 20, wherein the surrounding material is composed of said material substantially transparent for the predetermined radiation waves and is composed of predetermined pigments providing the non-transparency of the surrounding material.

23. The device according to claim 22, wherein said predetermined pigments include at least one from the following list: carbon, titanium oxide, BaS and $BaSO_4$.

24. The device according to claim 1, for use measuring the optical response of the measurement location to predetermined incident radiation.

25. The device according to claim 24, for use in occlusion-based non-invasive optical measurements, wherein over-systolic pressure is additionally applied to the patient's blood-perfused medium.

26. The device according to claim 1, for use in measuring the response in the form of an impedance resulting from an application of the external electrical field.

* * * * *